US008748185B2

(12) United States Patent
Horstmeyer

(10) Patent No.: US 8,748,185 B2
(45) Date of Patent: Jun. 10, 2014

(54) TEST MEDIUM FOR THE RAPID ANALYSIS OF MOTOR OILS IN INTERNAL COMBUSTION ENGINES

(76) Inventor: Gert Horstmeyer, Moersdorf (LU)

( * ) Notice: Subject to any disclaimer, the term of this patent is extended or adjusted under 35 U.S.C. 154(b) by 1019 days.

(21) Appl. No.: 11/721,264

(22) PCT Filed: Dec. 8, 2005

(86) PCT No.: PCT/EP2005/013162
§ 371 (c)(1),
(2), (4) Date: Sep. 1, 2009

(87) PCT Pub. No.: WO2006/061222
PCT Pub. Date: Jun. 15, 2006

(65) Prior Publication Data
US 2010/0206056 A1    Aug. 19, 2010

(30) Foreign Application Priority Data

Dec. 8, 2004 (DE) .......... 10-2004-059-020
Feb. 19, 2005 (DE) .......... 10-2005-028-025

(51) Int. Cl.
*G01N 15/00* (2006.01)
(52) U.S. Cl.
USPC ........... 436/60; 73/53.07; 73/53.05; 73/53.01
(58) Field of Classification Search
USPC ............ 436/60; 73/53.07, 53.05, 53.01
See application file for complete search history.

(56) References Cited

U.S. PATENT DOCUMENTS

| 2,302,224 | A | | 11/1942 | Jones | |
|---|---|---|---|---|---|
| 2,813,072 | A | * | 11/1957 | Biro | 522/178 |
| 5,132,225 | A | * | 7/1992 | Dickakian | 436/60 |
| 5,313,824 | A | | 5/1994 | Herguth et al. | |
| 5,817,928 | A | * | 10/1998 | Garvey et al. | 73/53.05 |
| 6,746,610 | B2 | * | 6/2004 | Manz et al. | 210/689 |

FOREIGN PATENT DOCUMENTS

| JP | 03-296408 | * | 12/1991 | ............ B01D 39/14 |
|---|---|---|---|---|
| JP | 03296408 | | 12/1991 | |
| JP | 04-004012 | * | 1/1992 | ............ B01D 39/16 |

OTHER PUBLICATIONS

Machine Translation of JP 03-296408. Obtained on Nov. 12, 2013. pp. 1-11.*

* cited by examiner

*Primary Examiner* — Christine T Mui
(74) *Attorney, Agent, or Firm* — Drinker Biddle & Reath LLP

(57) ABSTRACT

The present invention relates to a test medium for the rapid analysis of engine oils in internal combustion engines, having a weight per unit area of 50.0 to 200.0 g/m², comprising, based on the total weight of the test medium, 20.0% by weight to 98.0% by weight of cotton pulp, 0.0% by weight to 50.0% by weight of cellulose and 0.1% by weight to 50.0% by weight of silicic acid and/or at least one silicate salt. The present invention also relates to a method for the rapid analysis of engine oils in internal combustion engines, in which a drop of an engine oil to be analyzed is applied to the test medium according to the invention and is allowed to penetrate into the test medium, and the text result is then preferably compared with at least one reference image in order to determine the condition of the engine.

19 Claims, No Drawings

TEST MEDIUM FOR THE RAPID ANALYSIS OF MOTOR OILS IN INTERNAL COMBUSTION ENGINES

The present invention relates to a test medium for the rapid analysis of engine oils in internal combustion engines, and to a method for the rapid analysis of the present conditions of internal combustion engines using the test medium according to the invention.

Many objects in daily life, such as e.g. cars, motorbikes, diggers, ships, lawnmowers, are nowadays driven by internal combustion engines, with the condition of the internal combustion engine often having a critical influence on the usability and thus on the value of the object. It is usually possible only with great difficulty, if at all, to precisely assess the condition of an internal combustion engine, since this usually requires the dismantling of individual assemblies or the removal of the internal combustion engine and the dismantling thereof into its individual parts.

As an alternative, it is also possible in principle to assess the condition of the internal combustion engine indirectly. To this end, for example, a sample of the engine oil used in the internal combustion engine can be removed and analysed with regard to its composition in a suitable laboratory. A comparison of the final analysis result with the composition of the engine oil originally used then provides a useful indication with regard to the condition of the internal combustion engine. However, this procedure is extremely time-consuming and cost-intensive and is therefore usually not suitable in practice, for example when reselling the object.

Furthermore, regular checking of the engine condition allows the early detection of any defects or faults on the engine and it is usually less expensive to fix these defects than to purchase a new engine.

There is therefore a need for a simple, fast and inexpensive method for assessing the condition of an internal combustion engine.

A first approach to solving these problems is offered by the test paper COLUTEST® from the company Stratex. With this test paper, a drop of the engine oil to be analysed is applied to a test sheet made of cellulose and cotton and is allowed to penetrate into the paper. In this way, a chromatographic separation of the engine oil is obtained which can be used to detect impurities in the engine oil (carbon black, coolant, fuel) and changes in the engine oil (oxidation of the engine oil). However, one disadvantage of this test is the extremely long test duration of several hours, usually of up to 12 or even 24 hours, which is much too long for the rapid assessment of the condition of e.g. used cars that is required to practice. Furthermore, the test often leads to unclear and inaccurate results in the case of diesel engines.

In view of this prior art, the object of the present invention was therefore to provide better and faster possibilities for assessing the condition of internal combustion engines.

These and other objects which are not expressly mentioned but which can be derived as obvious from the contexts discussed herein or necessarily emerge therefrom are achieved by a test medium having all the features of the present claim 1. Advantageous modifications of the test medium according to the invention are described in the dependent claims which refer back to claim 1. The independent method claim protects a particularly advantageous procedure for the rapid analysis of engine oils in internal combustion engines. Particularly suitable variations of the method according to the invention are described in the dependent method claims.

By providing a test medium which has a weight per unit area of 50.0 to 200.0 g/m² and which comprises, based on the total weight of the test medium, 20.0% by weight to 98.0% by weight of cotton pulp, 0.0% by weight to 30.0% by weight of cellulose and 0.1% by weight to 50.0% by weight of silicic acid and/or at least one silicate, it is possible in a way that was not readily foreseeable to provide a test medium for the rapid analysis of engine oils in internal combustion engines which permits a relatively fast and easy assessment of the condition of internal combustion engines.

At the same time, the following further advantages are achieved by the solution according to the invention:

- The test medium according to the invention can be produced in a simple manner, on a large scale and inexpensively.
- The test medium according to the invention quickly provides results that can be clearly interpreted with regard to the condition of the engine oil and thus gives a fast and clear glance into the interior of the engine, as is otherwise possible only by means of complicated and expensive laboratory tests.
- The test medium according to the invention permits a relatively accurate analysis of the quality of the engine oil to be tested. Both ageing of the engine oil (increase in viscosity, oxidation) and contamination of the engine oil, in particular by combustion residues (carbon black), fuel, cooling liquid (water, glycol), can easily be detected. In this way, faults or defects on the internal combustion engine can be indicated and isolated.
- By analysing the engine oil with the aid of the test medium according to the invention, the user is given useful indications and information about any existing defects.
- By analysing the engine oil with the aid of the test medium according to the invention, the user can easily check whether or when a change of engine oil is necessary after a certain running time or running distance.
- The test medium according to the invention offers a simple and at the same time extremely effective possibility for checking the optimal efficiency and optimal combustion of the internal combustion engine. Disadvantageous effects on the environment caused by excessive fuel consumption or increased emissions of harmful substances can thus be avoided.
- The test medium according to the invention allows the rapid analysis of all engines which are operated with a lubricant (engine oil) and is also suitable in particular for the rapid analysis of diesel engines.

The test medium according to the invention has a weight per unit area in the range from 50.0 to 200.0 g/m², preferably in the range from 60.0 to 140.0 g/m², in particular in the range from 70.0 to 100.0 g/m².

It also comprises, based on the total weight of the test medium, 20.0% by weight to 98.0% by weight, preferably 45.0% by weight to 98.0% by weight, more preferably 60.0% by weight to 98.0% by weight, particularly preferably 65.0% by weight to 98.0% by weight, in particular 70.0% by weight to 98.0% by weight of cotton pulp, 0.0 to 50.0% by weight, preferably 0.0 to 25.0% by weight, more preferably 0.0 to 10.0% by weight, particularly preferably 0.0 to 5.0% by weight, in particular 0.0% by weight of cellulose, and 0.1% by weight to 50.0% by weight, preferably 0.5% by weight to 40.0% by weight, purposefully 1.0% by weight to 35.0% by weight, particularly preferably 2.0% by weight to 30.0% by weight, in particular 5.0% by weight to 30.0% by weight of silicic acid and/or at least one silicate.

According to one particularly preferred embodiment, the test medium contains, based on its total weight, at least 0.1% by weight of cellulose.

The above components are known per se. Cotton pulp is understood to mean the spinnable and non-spinnable seed hairs of the yellow-flowering cotton plant (*Gossypium*), which belongs to the mallow family and has been cultivated for more than 5000 years in tropical to sub-tropical climates.

Cellulose denotes the β-1,4-polyacetal of cellobiose. One embodiment of cellulose which is particularly preferred according to the invention is the wood-derived base material for paper production.

The silicates which can be used according to the invention include salts and esters, in particular salts (so-called silicic acid esters) of orthosilicic acid $[Si(OH)_4]$ and the condensation products thereof, such as for example nesosilicates (island silicates), inosilicates (chain silicates and band silicates), phyllosilicates (sheet silicates, layer silicates) and tectosilicates (framework silicates). Silicates which are particularly suitable according to the invention include aluminium silicate and calcium silicate. Good results can also be achieved using kaolin, china clay and/or Bullcaid (silicate-based aggregates), preferably in quantities of 5.0 to 30.0% by weight, based on the total weight of the medium. For further details, reference is hereby made to the customary specialist literature, in particular to Römpp-Lexikon Chemie; edited by: J. Falbe, M. Regitz; Stuttgart, New York; Thieme, 9th edition, keyword "Silicate" and the literature references cited therein.

Within the scope of the present invention, the silicates may be present both individually and in a mixture.

According to one particularly preferred embodiment of the present invention, the test medium contains at least one crosslinked silicic acid.

According to the invention, the medium contains, based on $0.031\ m^2$ of test medium, preferably 0.1 g to 2.0 g, in particular 0.1 g to 1.5 g, of silicic acid. According to a first particularly preferred variant of the present invention, the paper comprises, based on $0.031\ m^2$ of test medium, 0.1 g to 0.6 g of silicic acid. According to a further particularly preferred variant of the present invention, the paper comprises, based on $0.031\ m^2$ of test medium, 0.3 g to 1.5 g of silicic acid.

The silicate content of the medium, based on $0.031\ m^2$ of test medium, is advantageously in the range from 0.1 g to 1.5 g. According to a first particularly preferred embodiment of the present invention, the medium contains, based on $0.031\ m^2$ of test medium, 0.3 g to 0.9 g of aluminium silicate. According to a second particularly preferred embodiment of the present invention, the medium comprises, based on $0.031\ m^2$ of test medium, 0.1 g to 0.8 g of calcium silicate or another silicate. According to a third particularly preferred embodiment of the present invention, the medium comprises, based on $0.031\ m^2$ of test medium, 0.4 g to 1.0 g of calcium silicate.

For the purposes of the present invention, it is further preferred that the medium contains, based on $0.031\ m^2$ of test medium, 0.01 g to 0.1 g of binders and/or retention agents known per se. The binder is intended in particular to serve for sizing the test medium, i.e. for consolidating the fibre structure, for the binding of fillers and optionally of pigments, for increasing the water resistance and for improving the writeability and printability. The retention agent is added in particular to retain any fine substances and fillers during production.

Binders which are particularly suitable according to the invention include starch, casein, proteins, polymer dispersions and resin glues. According to the invention, aluminium sulphate and synthetic cationic substances have proven particularly suitable as retention agents.

Within the scope of the present invention, the test medium furthermore contains, based on $0.031\ m^2$ of test medium, 0.001 g to 0.1 g, in particular 0.01 g, of at least one defoamer. The compounds which can be used in this connection are sufficiently well known from the prior art and are not subject to any particular restrictions.

The production of the carrier materials according to the invention can take place in a manner known per se. It preferably comprises the following steps:

1. Substance Preparation

The materials are preferably supplied predominantly in dry form and are suspended in water in the pulper (substance hopper) to form the fibre pulp suitable for pumping. The fibrous material suspensions then run through preferably different stations for cleaning, refining (fibrillation and shortening of the fibres to the required length) and possibly classification (separation into different fibre lengths) before they are fed to the "central system". In the central system, the prepared fibrous material suspensions are mixed together with the paper auxiliaries (optionally also in liquid form) in a "mixing butt", preferably according to a recipe, to form the so-called stock. The latter preferably consists of 2.0 to 6.0% by weight of solids and 94.0 to 98.0% by weight of water and is preferably further diluted before being supplied to the paper machine.

2. Paper Machine

In the paper machine, a flat web is continuously produced from the highly diluted stock, and the water is removed by means of mechanical and thermal forces. For technical details, reference is hereby made to the specialist literature, in particular to Römpp-Lexikon Chemie; edited by: J. Falbe, M. Regitz; Stuttgart, New York; Thieme, 9th edition, keyword "Papier" (paper) and the literature references cited therein.

3. Finishing

The "machine-smooth" paper coming out of the paper machine is preferably finished with the aid of at least one coating installation and/or at least one calander. In the coating installation, the paper is provided with a binder-containing coating composition on one or both sides. In the calander, the paper surface is made smooth and glossy. For further details, reference is once again made to the specialist literature, in particular to Römpp-Lexikon Chemie; edited by: J. Falbe, M. Regitz; Stuttgart, New York; Thieme, 9th edition, keyword "Papier" (paper) and the literature references cited therein.

4. Trimming

The last process step during production is the cutting (referred to as trimming) of the large rolls coming from the paper machine or from the finishing area into the required formats. Further details can be found in the specialist literature, in particular in Römpp-Lexikon Chemie; edited by: J. Falbe, M. Regitz; Stuttgart, New York; Thieme, 9th edition, keyword "Papier" (paper) and the literature references cited therein.

Within the scope of a first particularly preferred embodiment of the present invention, the production of the test medium according to the invention takes place by mixing the cotton pulp and any cellulose and the silicic acid and/or the at least one silicate in the respectively desired quantities according to the above method to form a stock, and processing it to form a test paper.

According to a second particularly preferred embodiment of the present invention, the production of the test medium according to the invention takes place by producing a "machine-smooth paper" according to the method described above, which contains the necessary proportions of cotton pulp and optionally cellulose, and impregnating the latter in a special device with the required quantities of silicic acid and/or of the at least one silicate.

According to a third particularly preferred embodiment of the present invention, the production of the test medium according to the invention takes place by producing a "machine-smooth paper" according to the method described above, which contains the necessary proportions of cotton and optionally cellulose, and coating the latter with a coating composition which contains the required quantities of silicic acid and/or of the at least one silicate.

The use of the test medium according to the invention is immediately obvious to the person skilled in the art from the contexts described above. It is preferably used for the rapid analysis of the engine oil in an internal combustion engine, wherein a drop of the engine oil to be analysed is applied, preferably in spot form, to a test medium according to at least one of the preceding claims and is allowed to penetrate into the medium.

Even just by the rate of penetration, the present invention gives an indication of the condition of the engine oil, i.e. the faster the engine oil is drawn in, the better the condition of the engine oil (good viscosity), and the longer it takes to penetrate into the test medium the poorer the lubricating effect (high viscosity, i.e. poor condition of the engine oil). Accordingly, the penetration time taken for the engine oil to penetrate into the test medium is preferably measured in the method according to the invention.

By evaluating the resulting separation on the test medium, the person skilled in the art obtains useful information, in particular with regard to:
- the viscosity of the engine oil, which is preferably determined at least qualitatively;
- the degree of oxidation of the engine oil, which is preferably determined at least qualitatively;
- the carbon black content in the engine oil, which is preferably determined at least qualitatively;
- the water content in the engine oil, which is preferably determined at least qualitatively;
- the glycol content in the engine oil, which is preferably determined at least qualitatively;
- any dilution of the engine oil with fuel, which is preferably determined at least qualitatively;
- the dust content in the engine oil, which is preferably determined at least qualitatively.

For this purpose, the resulting separation of the respective oil components is preferably compared with at least one reference image. The reference images advantageously show the individual condition stages of the engine oil and make it possible for the person skilled in the art and the layman to draw the correct conclusions from the test carried out.

By way of example, combustion residues (carbon black in the engine oil) may indicate a poor setting of the carburettor, faulty injection, poor carburation, an incorrectly set injection pump, a poor air supply and/or an incorrect way of driving, which may lead to contamination of the engine and of the engine oil and also of the oil channels, to a reduction in working clearances, to heating of the upper engine part and/or to increased wear of friction surfaces.

A poor condition of engine oil may for example be attributed to engine oil that is too old, to the presence of cooling water in the engine oil and/or to the formation of metal particles, and may lead to a reduction in the viscosity of the engine oil, to acid attack on metal parts in the internal combustion engine (lead, copper, engine sump and lower parts) and/or to increased wear of the piston rings and cylinders.

Fuel components in the engine oil may be due to faulty injection, a poor setting of the carburettor, a defect of the injection nozzle opening, a poor ignition setting, contaminated intake air, driving at high revs with a cold engine and/or short journeys, which may lead to increased fuel consumption, to impairment of the timing chain, to dilution of the engine oil and thus to the risk of overheating of the upper engine area, to a reduction in the lubricating effect of the engine oil and/or to increased wear of friction surfaces (piston, cylinder).

Water and/or cooling liquid in the engine oil may be caused for example by a leaky cylinder head gasket, by porous seals (in particular the oil cooler gasket), by a leaky water cooling system, by contaminated intake air or by condensing water, for example due to a large number of short journeys. Possible consequences include oxidation of the engine oil, dilution of the engine oil, an increase in oil temperature and pressure and increased engine wear.

In all the cases described above, it is recommended to carry out a basic check of said possible causes and to change the engine oil. The test should be repeated after a running distance of approx. 100 to 500 km in order to ensure that the defects have been completely eliminated.

Advantageously, the rapid analysis of the engine oil is carried out in such a way that the resulting separation of the oil components is analysed 1 second to 180 minutes, preferably 1 minute to 120 minutes, in particular 2 minutes to 60 minutes, after the application of just one drop of engine oil. The results obtained are preferably documented so that it is possible to have an overview of the development of the internal combustion engine and to be able to react immediately to any deviations.

The test media contaminated with the engine oil can easily be collected and disposed of in an environmentally friendly manner.

Hereinbelow, the results of tests and comparative tests will be described without intending to limit the scope of the invention in any way.

As the carrier material, 100% cotton pulp with weights per unit area of 50 g/m$^2$ to 200 g/m$^2$ and in particular with weights per unit area of 60 g/m$^2$ to 140 g/m$^2$ were used for the most successful results to date.

The catalysts, accelerators and reactants are in the best results (weights based on a test sheet having a diameter of 200 mm):
- 0.3 g to 0.9 g of aluminium silicate, 0.1 g to 0.6 g of precipitated silicic acid, 0.01 g to 0.1 g of binders and retention agents, 0.01 g of defoamers.
- 0.3 g to 1.5 g of precipitated silicic acids and 0.1 g to 0.8 g of calcium silicate, 0.01 g to 0.1 g of binders and retention agents, 0.01 g of defoamers. Some silicic acids were specially crosslinked due to the high level of hydrophobicity.
- 0.4 g to 1.0 g of calcium silicate, 0.01 g to 0.1 g of retention agents and binders and defoamers.

Good results were also achieved with cotton papers, 140 g/m$^2$, with the addition of in each case 5-30% by weight kaolin, china clay and/or Bullcaid, wherein the penetration times were good but the maturing processes were relatively slow.

The results achieved were assessed with respect to the possibilities of the test sheets of manufacturers from the prior art. These are papers which consist of cellulose and cotton, namely in a ratio of 90:10 or 80:20. In these media, the end results were usually not obtained until after 10 to 24 hours had passed. In older, used engine oils, the penetration time of the oils was extremely long, up to several hours. The end results with engine oils from diesel vehicles were also too undefined and were not clear enough at the transitions.

Commercially available laboratory filter papers can be easily compared with the test medium according to the invention;

they have similar properties to the described test sheets of the prior art. Here, numerous paper types and qualities, inter alia from Schleicher & Schüll and from Macherei Nagel, were tested. Here, too, the penetration and maturing times were very long especially in the case of old oils, and the diesel engine oils were again too unclear.

From the end results, the tests with TLC plates and TLC papers (Thin Layer Chromatography) based on aluminium silicates and silicic acids and silica gel proved to be advantageous. Here too, however, the drying time proved to be unacceptable since especially older and used oils did not dry even after days.

In terms of the end result, inkjet papers also showed good results in the separation of the oil components, but the drying and maturing times of these too, like the TLC aluminium films and many dense papers, were much too slow; the times were between 1 hour and several days.

The assessment criteria for the tests (in protocols from 0=poor to 10=very good) were as follows:
- penetration time of the engine oil (not the final drying of the engine oil!)
- separation of the components (carbon black)
- detection of the viscosity
- formation of light rings (fuel in the oil)
- point formation at the edge (water in the oil) and formation of a corona (glycol)
- streak formation in the end result (after final drying)

For the products according to the invention, these times were in the following ranges:

| | |
|---|---|
| penetration time of the engine oil | 2 to 30 minutes |
| separation of the components (carbon black) | 2 to 60 minutes |
| detection of the viscosity | 5 to 30 minutes |
| formation of light rings (fuel in the oil) | 2 to 30 minutes |
| point formation at the edge (water in the oil) | 1 to 60 minutes |
| formation of a corona (glycol) | 30 to 180 minutes |

Depending on the condition of the respective oil, the streak formation takes place after a few hours, since the final drying of the oil must have taken place for these results.

The invention claimed is:

1. A paper test medium for the rapid analysis of engine oils in internal combustion engines comprising, based on the total weight of said paper test medium, 70.0% by weight to 98.0% by weight of cotton pulp, 0.0% by weight to 50.0% by weight of cellulose, and 0.5% by weight to 30.0% by weight of silicic acid and/or at least one silicate, wherein said paper test medium has a weight per unit area of 50.0 to 200.0 g/m$^2$ and is coated with said silicic acid and/or at least one silicate.

2. The test medium according to claim 1, wherein the test medium contains, based on 0.031 m$^2$ of test medium, 0.1 g to 2.0 g of silicic acid.

3. The test medium according to claim 1 wherein the test medium contains, based on 0.031 m$^2$ of test medium, 0.1 g to 1.5 g of at least one silicate.

4. The test medium according to claim 1, wherein the test medium contains aluminum silicate and/or calcium silicate.

5. The test medium according to claim 1, wherein the test medium contains, based on 0.031 m$^2$ of test medium, 0.01 to 0.1 g of binder and/or retention agent.

6. The test medium according to claim 1, wherein the test medium contains, based on 0.031 m2 of test medium, 0.001 g to 0.1 g of at least one defoamer.

7. A method for the rapid analysis of engine oils in internal combustion engines, in which a drop of an engine oil to be analysed is applied to a test medium according to at least one of the preceding claims and is allowed to penetrate into the test medium, wherein the components of said engine oil are separated.

8. The method according to claim 7, wherein the engine oil is applied to the test medium in spot form.

9. The method according to claim 7 wherein the penetration time taken for the engine oil to penetrate into the test medium is measured.

10. The method according to claim 7, wherein the resulting separation of the oil components is evaluated.

11. The method according to claim 10, wherein the resulting separation of the oil components is compared with at least one reference image.

12. The method according to claim 10 wherein the resulting separation of the oil components is evaluated 1 second to 60 minutes after the application of the engine oil.

13. The method according to claim 7, wherein the viscosity of the engine oil is determined at least qualitatively.

14. The method according to claim 7, wherein the degree of oxidation of the engine oil is determined at least qualitatively.

15. The method according to claim 7, wherein the carbon black content in the engine oil is determined at least qualitatively.

16. The method according to claim 7, wherein the water content in the engine oil is determined at least qualitatively.

17. The method according to claim 7, wherein the glycol content in the engine oil is determined at least qualitatively.

18. The method according to claim 7, wherein any dilution of the engine oil with fuel is determined at least qualitatively.

19. The method according to claim 7, wherein the dust content in the engine oil is determined at least qualitatively.

* * * * *